(12) United States Patent
Hung et al.

(10) Patent No.: US 8,278,550 B2
(45) Date of Patent: Oct. 2, 2012

(54) RUTHENIUM COMPLEX AND PHOTOELECTRIC COMPONENT USING THE SAME

(75) Inventors: Chiu-Ming Hung, Taoyuan Hsien (TW); Li-Ya Huang, Taoyuan Hsien (TW)

(73) Assignee: Everlight USA, Inc., Pineville, NC (US)

( * ) Notice: Subject to any disclaimer, the term of this patent is extended or adjusted under 35 U.S.C. 154(b) by 193 days.

(21) Appl. No.: 12/591,768

(22) Filed: Dec. 1, 2009

(65) Prior Publication Data

US 2011/0083732 A1 Apr. 14, 2011

(30) Foreign Application Priority Data

Oct. 8, 2009 (TW) ................ 98134108 A

(51) Int. Cl.
*H01L 31/00* (2006.01)
(52) U.S. Cl. ............... 136/256; 136/263; 546/12; 8/636
(58) Field of Classification Search .................. 136/263, 136/256; 546/12; 8/636
See application file for complete search history.

(56) References Cited

U.S. PATENT DOCUMENTS

| | | | | |
|---|---|---|---|---|
| 6,586,670 B2 * | 7/2003 | Yoshikawa | ..................... | 136/263 |
| 7,091,138 B2 * | 8/2006 | Numasawa et al. | ........... | 438/778 |
| 7,118,936 B2 * | 10/2006 | Kobayashi et al. | ............. | 438/99 |
| 7,202,412 B2 * | 4/2007 | Yamanaka et al. | ............. | 136/263 |
| 7,538,217 B1 * | 5/2009 | Lin et al. | ............................ | 546/2 |
| 2004/0248394 A1 * | 12/2004 | Kobayashi et al. | ............ | 438/609 |
| 2006/0237059 A1 * | 10/2006 | Kurihara et al. | ............... | 136/263 |
| 2007/0044835 A1 * | 3/2007 | Yoshimoto et al. | ............. | 136/263 |
| 2008/0110496 A1 * | 5/2008 | Jung et al. | ...................... | 136/256 |
| 2009/0216021 A1 * | 8/2009 | Jiang et al. | ....................... | 546/12 |
| 2010/0101643 A1 * | 4/2010 | Takahashi et al. | ............. | 136/256 |
| 2010/0180949 A1 * | 7/2010 | Takahashi et al. | ............. | 136/263 |

* cited by examiner

*Primary Examiner* — Mark Eashoo
*Assistant Examiner* — M. Reza Asdjodi
(74) *Attorney, Agent, or Firm* — Bacon & Thomas, PLLC

(57) ABSTRACT

The present invention relates to a ruthenium complex and a photoelectric component using the same, and the ruthenium complex is represented by the following formula (I):

$$RuL_1L_2(NCS)_2A_m \quad (I)$$

wherein $L_1$, $L_2$, A and X are defined the same as the specification. The ruthenium complex of the present invention is suitable for a Dye-Sensitized Solar Cell (DSC). Hence, the photoelectric characteristics of the DSC manufactured with the ruthenium complex of the present invention are an improvement.

2 Claims, No Drawings

RUTHENIUM COMPLEX AND PHOTOELECTRIC COMPONENT USING THE SAME

BACKGROUND OF THE INVENTION

1. Field of the Invention

The present invention relates to a ruthenium complex and a photoelectric component using the same and, more particularly, to a ruthenium complex, which is used for the dye-sensitized solar cell (DSC), and a photoelectric component using the same.

2. Description of Related Art

With the advance of industrial technology, the whole world is today facing two very serious problems, the energy crisis and the environmental pollution. One of the effective means to solve the global energy crisis and to reduce the environmental pollution is the solar cell, which can convert solar energy into electricity. Since the dye-sensitized solar cell has the advantages of low manufacturing cost, large-scale production, great flexibility, light transmittance, and being capable of incorporation in buildings, the application of the dye-sensitized solar cell has become more and more attractive.

Recently, Grätzel et al. disclosed a series of publications (for example, O'Regan, B.; Grätzel, M. *Nature* 1991, 353, 737), which show the practicability of the dye-sensitized solar cell. The general structure of the dye-sensitized solar cell comprises an anode, a cathode, a nano-porous titanium dioxide layer, a dye, and electrolyte, wherein the dye plays a critical role in the conversion efficiency of the dye-sensitized solar cell. The dye suitable for the dye-sensitized solar cell must have characteristics in broad absorption spectrum, high molar absorption coefficient, thermal stability, and light stability.

Grätzel's lab has published a series of ruthenium complexes as the dyes for the dye-sensitized solar cell. In 1993, Grätzel's lab published a dye-sensitized solar cell prepared with an N3 dye, and the conversion efficiency of the dye-sensitized solar cell is 10.0% under the illumination of AM 1.5 stimulated light. The incident photon-to-current conversion efficiency (IPCE) value of the N3 dye is 80% in the range of 400 to 600 nm. Although hundreds of ruthenium complexes have been developed, the conversion efficiency of those dye complexes is not as good as that of the N3 dye. The structure of the N3 dye is represented by the following formula (a).

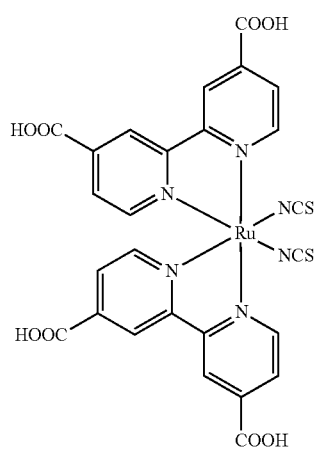

In 2003, Grätzel's lab published details of a dye-sensitized solar cell prepared with an N719 dye, and the conversion efficiency of the dye-sensitized solar cell is improved to 10.85% under the illumination of AM 1.5 stimulated light, wherein the structure of the N719 dye is represented by the following formula (b).

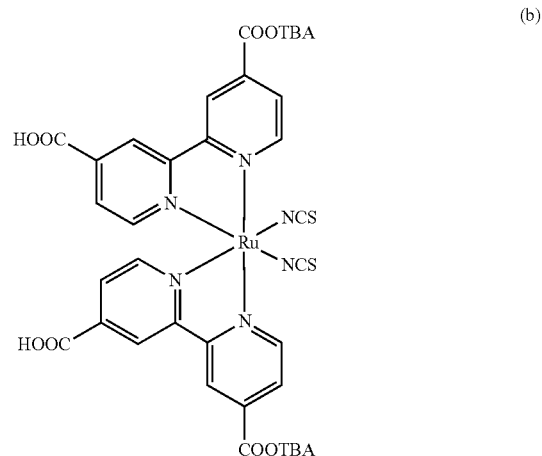

Grätzel's lab also published a dye-sensitized solar cell prepared with a black dye in 2004, and the conversion efficiency of the dye-sensitized solar cell is 11.04% under the illumination of AM 1.5 stimulated light. The black dye can enhance the spectral response in red and near-IR region, so the conversion efficiency of the dye-sensitized solar cell can be improved. The structure of the black dye is represented by the following formula (c).

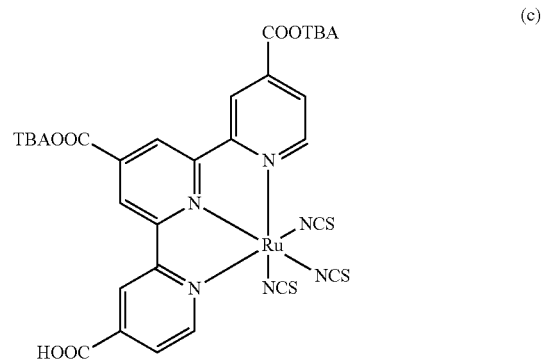

Except the ruthenium complexes such as the N3 dye, the N719 dye, and the black dye, other compounds able to be used in the dye-sensitized solar cell are platinum complexes, osmium complexes, iron complexes, and copper complexes. However, the results of various studies show that the conversion efficiency of the ruthenium complexes is still better than other types of dye compounds.

The dyes for the dye-sensitized solar cell greatly influence the conversion efficiency. Hence, it is desirable to provide a dye compound, which can improve the conversion efficiency of the dye-sensitized solar cell.

SUMMARY OF THE INVENTION

The present invention is to provide a novel ruthenium complex, which is used for a dye-sensitized solar cell to improve the photoelectric efficiency of the dye-sensitized solar cell.

The present invention is also to provide a dye-sensitized solar cell, which has excellent photoelectric property.

Hence, the present invention provides a ruthenium complex, which is represented by the following formula (I):

$$RuL_1L_2(NCS)_2A_m \qquad (I)$$

wherein $L_1$ is 2,2'-bipyridyl-4,4'-dicarboxylic acid, 2,2'-bipyridyl-4,4'-disulfonic acid, or 2,2'-bipyridyl-4,4'-diphosphonic acid;

$L_2$ is 2,2'-bipyridyl-4,4'-dinonyl, or 2,2'-bipyridine-4,4'-ditridecyl;

A is $X^+R_1R_2R_3R_4$,

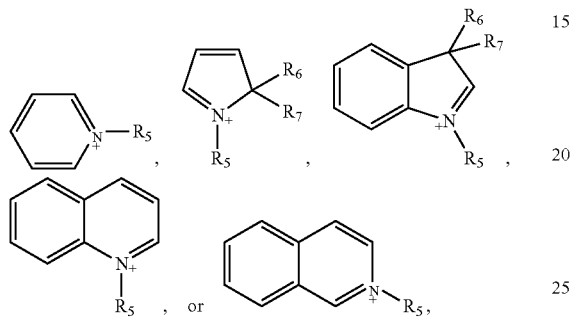

wherein X is N, or P, $R_1$, $R_2$, $R_3$, and $R_4$ are each independently $C_{1-20}$ alkyl, phenyl, or benzyl, and $R_5$, $R_6$, $R_7$ are each independently $C_{1-20}$ alkyl; and m is 1, or 2.

In the above formula (I), $L_1$ may be 2,2'-bipyridyl-4,4'-dicarboxylic acid, 2,2'-bipyridyl-4,4'-disulfonic acid, or 2,2'-bipyridyl-4,4'-diphosphonic acid. Preferably, $L_1$ is 2,2'-bipyridyl-4,4'-dicarboxylic acid.

In the above formula (I), $L_2$ may be 2,2'-bipyridyl-4,4'-dinonyl, or 2,2'-bipyridine-4,4'-ditridecyl. Preferably, $L_2$ is 2,2'-bipyridyl-4,4'-dinonyl.

In the above formula (I), A is $X^+R_1R_2R_3R_4$,

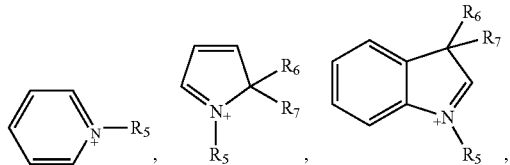

wherein X is N, or P, $R_1$, $R_2$, $R_3$, and $R_4$ are each independently $C_{1-20}$ alkyl, phenyl, or benzyl, and $R_5$, $R_6$, $R_7$ are each independently $C_{1-20}$ alkyl. Preferably, A is $P^+R_1R_2R_3R_4$, wherein $R_1$, $R_2$, $R_3$, and $R_4$ are each independently $C_{1-20}$ alkyl, phenyl, or benzyl. More preferably, A is $N^+R_1R_2R_3R_4$, wherein $R_1$, $R_2$, $R_3$, and $R_4$ are each independently $C_{1-20}$ alkyl, phenyl, or benzyl. Most preferably, A is $N^+R_1R_2R_3R_4$, wherein $R_1$, $R_2$, $R_3$, and $R_4$ are each independently $C_{1-20}$ alkyl, phenyl, or benzyl.

In the above formula (I), m may be 1, or 2. Preferably, m is 1.

The specific examples of ruthenium complex represented by the above formula (I) are:

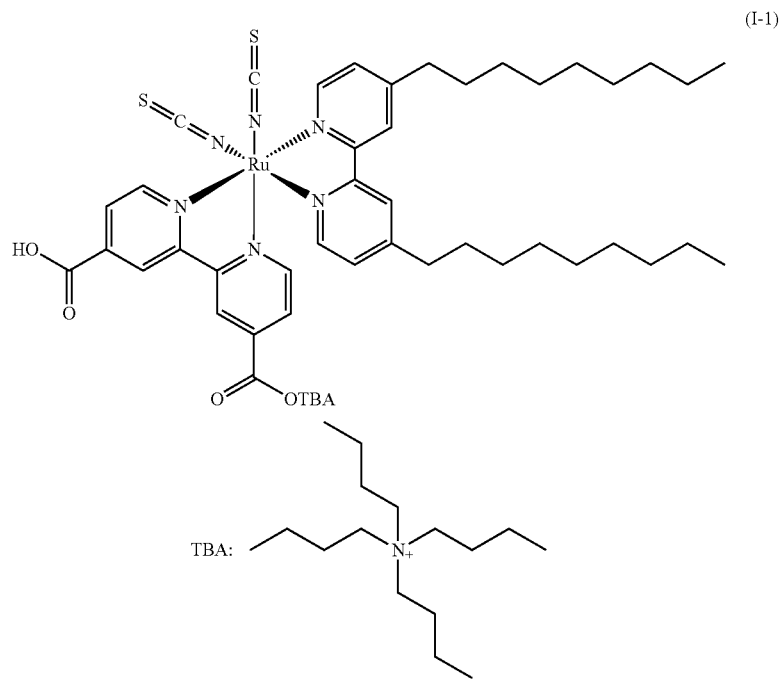

(I-1)

-continued
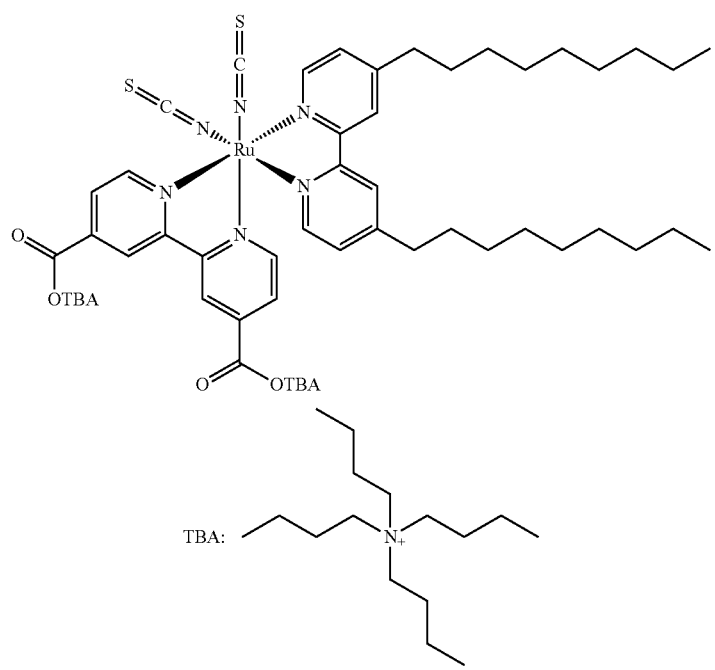
(I-2)
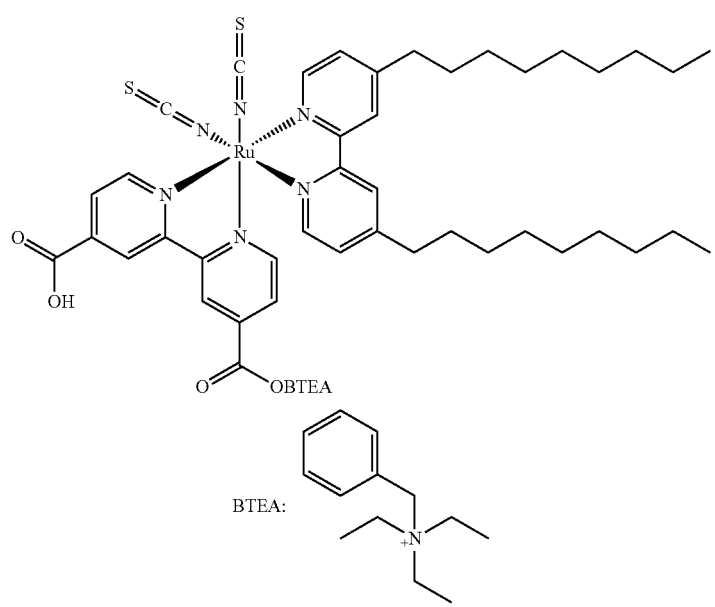
(I-3)

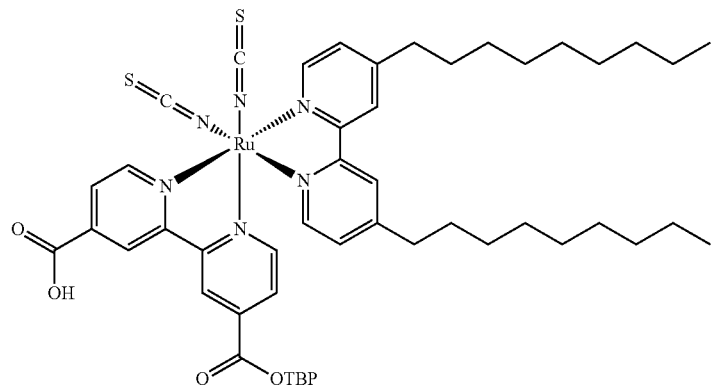
(I-4)
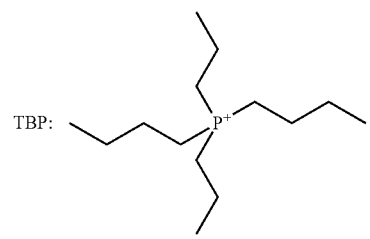
TBP:
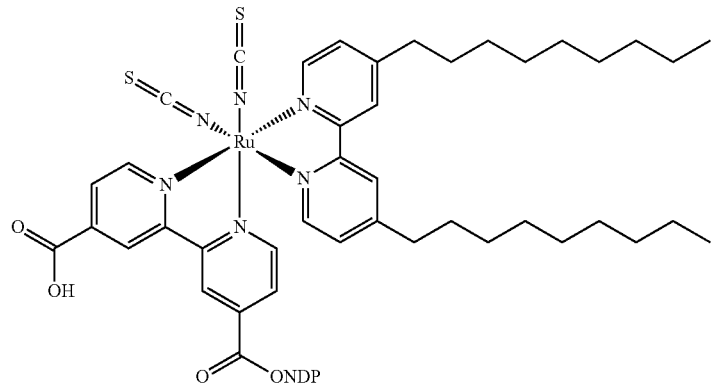
(I-5)
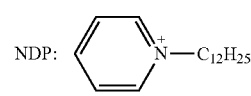
NDP:
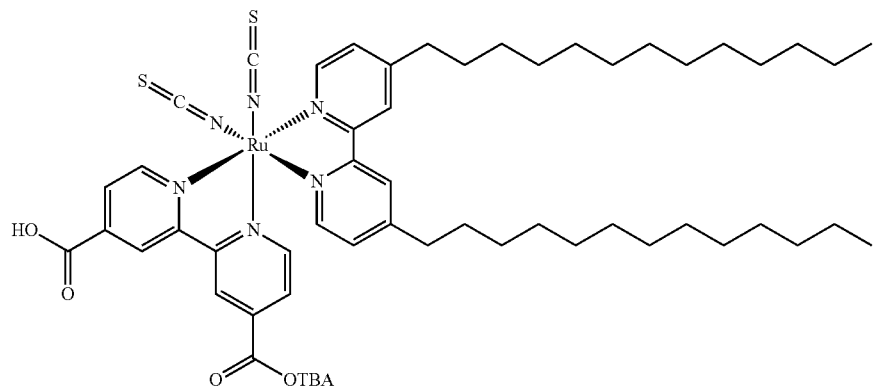
(I-6)

The present invention also provides a dye-sensitized solar cell, which comprises the aforementioned ruthenium complex.

In addition, the dye-sensitized solar cell of the present invention comprises: (a) a photoanode comprising the aforementioned ruthenium complex; (b) a cathode; and (c) an electrolyte layer disposed between the photoanode and the cathode.

In the dye-sensitized solar cell of the present invention, the photoanode comprises: a transparent substrate, a transparent conductive layer, a porous semiconductive layer, and a dye of the ruthenium complex.

In the dye-sensitized solar cell of the present invention, the material of the transparent substrate for the photoanode is not particularly limited, as long as the material of the substrate is a transparent material. Preferably, the material of the transparent substrate is a transparent material with good moisture resistance, solvent resistance and weather resistance. Thus, the dye-sensitized solar cell can resist moisture or gas from outside by the transparent substrate. The specific examples of the transparent substrate include, but are not limited to, transparent inorganic substrates, such as quartz and glass; transparent plastic substrates, such as poly(ethylene terephthalate) (PET), poly(ethylene 2,6-naphthalate) (PEN), polycarbonate (PC), polyethylene (PE), polypropylene (PP), and polyimide (PI). Additionally, the thickness of the transparent substrate is not particularly limited, and can be changed according to the transmittance and the demands for the properties of the dye-sensitized solar cell. Preferably, the material of the transparent substrate is glass.

Furthermore, in the dye-sensitized solar cell of the present invention, the material of the transparent conductive layer can be indium tin oxide (ITO), fluorine-doped tin oxide (FTO), $ZnO$—$Ga_2O_3$, $ZnO$—$Al_2O_3$, or tin-based oxides.

In addition, in the dye-sensitized solar cell of the present invention, the porous semiconductive layer can be made of semiconductor particles. Suitable semiconductor particles may include Si, $TiO_2$, $SnO_2$, ZnO, $WO_3$, $Nb_2O_5$, $TiSrO_3$, and the combination thereof. Preferably, the semiconductor particles are $TiO_2$ particles. The average diameter of the semiconductor particles may be 5 to 500 nm. Preferably, the average diameter of the semiconductor particles is 10 to 50 nm. Furthermore, the thickness of the porous semiconductive layer is 5-25 μm.

In the dye-sensitized solar cell of the present invention, the ruthenium complex may be the aforementioned ruthenium complex.

Besides, the material of the cathode for the dye-sensitized solar cell is not particularly limited, and may include any material with conductivity. Otherwise, the material of the cathode can be an insulating material, as long as there is a conductive layer formed on the surface of the cathode facing the photoanode. The material of the cathode can be a material with electrochemical stability. The unlimited examples suitable for the material of the cathode include Pt, Au, C, or the like.

Furthermore, the material used in the electrolyte layer of the dye-sensitized solar cell is not particularly limited, and can be any material, which can transfer electrons and/or holes.

In addition, the present invention further provides a dye solution, which comprises the aforementioned ruthenium complex.

The dye solution of the present invention comprises: (A) 0.01-1 wt % of the aforementioned ruthenium complex; and (B) 99-99.99 wt % of organic solvent, which is selected from the group consisting of acetonitrile, methanol, ethanol, propanol, butanol, dimethyl formamide, and N-methyl-2-pyrrolidinone.

Other objects, advantages, and novel features of the invention will become more apparent from the following detailed description.

DETAILED DESCRIPTION OF THE PREFERRED EMBODIMENT

The ruthenium complex of the present invention can be synthesized by the following methods.

cis-di(thiocyanato)(2,2'-bipyridyl-4,4'-dicarboxylic acid) (2,2'-bi-pyridyl-4,4'-dinonyl)ruthenium(II) (Z907 dye) is synthesized according to the method described in *Nature Material*, 2003, 2, 402-407.

cis-di(thiocyanato)(2,2'-bipyridyl-4,4'-dicarboxylic acid) (2,2'-bi-pyridyl-4,4'-dinonyl)ruthenium(II) is dispersed in distilled water, and 10% aqueous solution of tetrabutylammonium hydroxide is added thereto to adjust the pH value of the reaction solution to 11. Then, the reaction solution is stirred until the ruthenium complex is dissolved in water completely. Finally, the pH value of the reaction solution is adjusted to 4.6 with 0.1 M nitric $acid_{(aq)}$ to obtain the ruthenium complex represented by the formula (I-1).

The method for manufacturing the dye-sensitized solar cell of the present invention is not particularly limited, and the dye-sensitized solar cell of the present invention can be manufacture by the conventional methods known in the art.

The material of the transparent substrate is not particularly limited, as long as the material of the substrate is a transparent material. Preferably, the material of the transparent substrate is a transparent material with good moisture resistance, solvent resistance and weather resistance. Thus, the dye-sensitized solar cell can resist moisture or gas from outside by the transparent substrate. The specific examples of the transparent substrate include, but are not limited to, transparent inorganic substrates, such as quartz and glass; transparent plastic substrates, such as poly(ethylene terephthalate) (PET), poly(ethylene 2,6-naphthalate) (PEN), polycarbonate (PC), polyethylene (PE), polypropylene (PP), and polyimide (PI). Additionally, the thickness of the transparent substrate is not particularly limited, and can be changed according to the transmittance and the demands for the properties of the dye-sensitized solar cell. In a specific embodiment, the material of the transparent substrate is a glass substrate.

Furthermore, the material of the transparent conductive layer can be indium tin oxide (ITO), fluorine-doped tin oxide (FTO), $ZnO$—$Ga_2O_3$, $ZnO$—$Al_2O_3$, or tin-based oxides. In a specific embodiment, fluorine-doped tin oxide is used for the transparent conductive layer.

In addition, the porous semiconductive layer is made of semiconductor particles. Suitable semiconductor particles may include Si, $TiO_2$, $SnO_2$, ZnO, $WO_3$, $Nb_2O_5$, $TiSrO_3$, and the combination thereof. First, the semiconductor particles are prepared in a form of paste, and then the transparent conductive substrate is coated with the paste. The coating method used herein can be blade coating, screen printing, spin coating, spray coating, or wetting coating. Additionally, the coating can be held for one time or many times, in order to obtain a porous semiconductive layer with suitable thickness. The semiconductive layer can be a single layer or multiple layers, wherein each layer of the multiple layers is formed by semiconductor particles with different diameters. For example, the semiconductor particles with diameters of 5 to 50 nm is coated in a thickness of 5 to 20 μm, and then the semiconductor particles with diameters of 200 to 400 nm are coated in a thickness of 3 to 5 μm thereon. After drying the coated substrate at 50-100° C., the coated substrate is sintered at 400-500° C. for 30 min to obtain a multilayer semiconductive layer.

The ruthenium complex can be dissolved in a suitable solvent to prepare a dye solution. Suitable solvents include, but are not limited to, acetonitrile, methanol, ethanol, propanol, butanol, dimethyl formamide, N-methyl-2-pyrrolidinone, or the combination thereof. Herein, the transparent substrate coated with the semiconductive layer is dipped into a dye solution to make the semiconductive layer absorb the dye in the dye solution completely. After the dye absorption is completed, the transparent substrate coated with the semiconductive layer is taken out and dried to obtain a photoanode for a dye-sensitized solar cell.

Besides, the material of the cathode for the dye-sensitized solar cell is not particularly limited, and may include any material with conductivity. Otherwise, the material of the cathode can be an insulating material, as long as there is a conductive layer formed on the surface of the cathode facing the photoanode. The material of the cathode can be a material with electrochemical stability. The unlimited examples suitable for the material of the cathode include Pt, Au, C, or the like.

Furthermore, the material used in the electrolyte layer of the dye-sensitized solar cell is not particularly limited, and can be any material, which can transfer electrons and/or holes. In addition, the liquid electrolyte can be a solution of acetonitrile containing iodine, a solution of N-methyl-2-pyrrolidinone containing iodine, or a solution of 3-methoxy propionitrile containing iodine. In a specific embodiment, the liquid electrolyte can be a solution of acetonitrile containing iodine.

One specific method for manufacturing the dye-sensitized solar cell of the present invention is presented as follows.

First, a glass substrate covered with fluorine-doped tin oxide (FTO) is coated with a paste containing $TiO_2$ particles with diameter of 20~30 nm for one time or several times by a screen printing process. Then, the coated glass substrate is sintered at 450° C. for 30 min.

The ruthenium complex is dissolved in a mixture of acetonitrile and t-butanol (1:1 v/v) to formulate a dye solution of a ruthenium complex. Then, the aforementioned glass substrate with porous $TiO_2$ layer is dipped into the dye solution. After the porous $TiO_2$ layer absorbs the dye in the dye solution, the resulting glass substrate is taken out and dried to obtain a photoanode.

A glass substrate covered with fluorine-doped tin oxide is drilled to form an inlet with a diameter of 0.75 μm, wherein the inlet is used for injecting the electrolyte. Then, a solution of $H_2PtCl_6$ is coated on the glass substrate covered with fluorine-doped tin oxide, and the glass substrate is heated to 400° C. for 15 min to obtain a cathode.

Sequentially, a thermoplastic polymer layer with a thickness of 60 μm is disposed between the photoanode and the cathode. These two electrodes are pressed at 120 to 140° C. to adhere with each other.

Then, an electrolyte is injected, wherein the electrolyte is a solution of acetonitrile containing 0.03 M $I_2$/0.3 M LiI/0.5 M t-butyl-pyridine. After the inlet is sealed with thermoplastic polymer layer, a dye-sensitized solar cell of the present invention is obtained.

The following examples are intended for the purpose of illustration of the present invention. However, the scope of the present invention should be defined as the claims appended hereto, and the following examples should not be construed as in any way limiting the scope of the present invention. Without specific explanations, the unit of the parts and percentages used in the examples is calculated by weight, and the temperature is represented by Celsius degrees (° C.). The relation between the parts by weight and the parts by volume is just like the relation between kilogram and liter.

Embodiment 1

Synthesis of cis-di(thiocyanato)(2,2'-bipyridyl-4,4'-dicarboxylic acid) (2,2'-bipyridyl-4,4'-dinonyl)ruthenium(II) (tetrabutylammonium) (I-1)

1 part of cis-di(thiocyanato)(2,2'-bipyridyl-4,4'-dicarboxylic acid) (2,2'-bipyridyl-4,4'-dinonyl)ruthenium(II) (Z907 dye) prepared according to the method described in *Nature Material*, 2003, 2, 402-407, and 10 parts of deionized water were added into a reaction flask, and the reaction solution was stirred to disperse the ruthenium complex. Then, 10% aqueous solution of tetrabutylammonium hydroxide was added into the reaction solution drop by drop to adjust the pH value of the reaction solution to 11. The reaction solution was stirred continuously, until the ruthenium complex was completely dissolved in the water. Then, 0.1 M nitric acid$_{(aq)}$ was used to adjust the pH value of the reaction solution to 4.6. After stirring the reaction solution for 18 hrs, the sintered glass filter was used for filtering the product out, followed by using 5 parts of distilled water with pH 4.1 to wash the product. Finally, 0.43 parts of black solid product (I-1) was obtained, and the yield of the product (I-1) was 85%.

Embodiment 2

Synthesis of cis-di(thiocyanato)(2,2'-bipyridyl-4,4'-dicarboxylic acid) (2,2'-bipyridyl-4,4'-dinonyl)ruthenium(II) bis(tetrabutylammonium) (I-2)

1 part of cis-di(thiocyanato)(2,2'-bipyridyl-4,4'-dicarboxylic acid) (2,2'-bipyridyl-4,4'-dinonyl)ruthenium(II) (Z907 dye) prepared according to the method described in *Nature Material*, 2003, 2, 402-407, and 10 parts of deionized water were added into a reaction flask, and the reaction solution was stirred to disperse the ruthenium complex. Then, 10% aqueous solution of tetrabutylammonium hydroxide was added into the reaction solution drop by drop to adjust the pH value of the reaction solution to 11. The reaction solution was stirred continuously, until the ruthenium complex was completely dissolved in the water. Then, 0.1 M nitric acid$_{(aq)}$ was used to adjust the pH value of the reaction solution to 5.5. After stirring the reaction solution for 18 hrs, the sintered glass filter was used for filtering the product out, followed by using 5 parts of distilled water with pH 4.1 to wash the product. Finally, 0.44 parts of black solid product (I-2) was obtained, and the yield of the product (I-2) was 70%.

Embodiment 3

Synthesis of cis-di(thiocyanato)(2,2'-bipyridyl-4,4'-dicarboxylic acid) (2,2'-bipyridyl-4,4'-dinonyl)ruthenium(II) (benzyltriethylammonium) (I-3)

The compound of the present embodiment was synthesized by the same method illustrated in Embodiment 1, except that 10 parts of deionized water was substituted with 5 parts of deionized water and 5 parts of methanol, and the aqueous solution of tetrabutylammonium hydroxide was substituted with an aqueous solution of benzyltriethylammonium hydroxide (TCI Co., Ltd.,). Finally, 0.35 parts of black solid product (I-3) was obtained, and the yield of the product (I-3) was 71%.

Embodiment 4

Synthesis of cis-di(thiocyanato)(2,2'-bipyridyl-4,4'-dicarboxylic acid) (2,2'-bipyridyl-4,4'-dinonyl)ruthenium(II) (tetrabutylphosphonium) (I-4)

The compound of the present embodiment was synthesized by the same method illustrated in Embodiment 1, except that 10 parts of deionized water was substituted with 5 parts of deionized water and 5 parts of methanol, and the aqueous solution of tetrabutylammonium hydroxide was substituted with aqueous solution of tetrabutylphosphonium hydroxide. Finally, 0.42 parts of black solid product (I-4) was obtained, and the yield of the product (I-4) was 81%.

Embodiment 5

Synthesis of cis-di(thiocyanato)(2,2'-bipyridyl-4,4'-dicarboxylic acid) (2,2'-bipyridyl-4,4'-dinonyl)ruthenium(II) (1-dodecylpyridinium) (I-5)

The compound of the present embodiment was synthesized by the same method illustrated in Embodiment 1, except that 10 parts of deionized water was substituted with 5 parts of deionized water and 5 parts of methanol, and the aqueous solution of tetrabutylammonium hydroxide was substituted with aqueous solution of 1-dodecylpyridinium hydroxide, which was formulated by 98% of 1-dodecylpyridinium chloride reagent (ALDRICH). Finally, 0.32 parts of black solid product (I-5) was obtained, and the yield of the product (I-5) was 63%.

Embodiment 6
Preparation of a Dye-Sensitized Solar Cell

A glass substrate covered with fluorine-doped tin oxide (FTO) was coated with a paste containing $TiO_2$ particles with diameter of 20~30 nm for one time or several times, wherein the thickness of the glass substrate was 4 mm and the electric resistance of the glass substrate is 10Ω. Then, the coated glass substrate was sintered at 450° C. for 30 min, and the thickness of the sintered porous $TiO_2$ layer was 10 to 12 μm.

The ruthenium complex prepared by Embodiment 1 was dissolved in a mixture of acetonitrile and t-butanol (1:1 v/v), and a dye solution containing 0.5 M ruthenium complex was obtained. Then, the aforementioned glass substrate covered with porous $TiO_2$ layer was dipped into the dye solution to make the dye adhered on the porous $TiO_2$ layer. After 16 to 24 hours, the resulting glass substrate was taken out and dried, and then a photoanode was obtained.

A glass substrate covered with fluorine-doped tin oxide was drilled to form an inlet with a diameter of 0.75 μm, wherein the inlet was used for injecting the electrolyte. Then, a solution of $H_2PtCl_6$ (2 mg Pt in 1 ml ethanol) was coated on the glass substrate covered with fluorine-doped tin oxide, and the resulting glass substrate was heated to 400° C. for 15 min to obtain a cathode.

Sequentially, a thermoplastic polymer layer with a thickness of 60 μm was disposed between the photoanode and the cathode. These two electrodes were pressed at 120 to 140° C. to adhere with each other.

Then, an electrolyte was injected, which was a solution of acetonitrile containing 0.03 M $I_2$/0.3 M LiI/0.5 M t-butylpyridine. After the inlet was sealed with thermoplastic polymer layer, a dye-sensitized solar cell of the present embodiment was obtained.

Embodiment 7
Preparation of a Dye-Sensitized Solar Cell

The process for preparing the dye-sensitized solar cell of the present embodiment was the same as that described in Embodiment 6, except that the ruthenium complex prepared by Embodiment 1 was substituted with the ruthenium complex prepared by Embodiment 2.

Embodiment 8
Preparation of a Dye-Sensitized Solar Cell

The process for preparing the dye-sensitized solar cell of the present embodiment was the same as that described in Embodiment 6, except that the ruthenium complex prepared by Embodiment 1 was substituted with the ruthenium complex prepared by Embodiment 3.

Embodiment 9
Preparation of a Dye-Sensitized Solar Cell

The process for preparing the dye-sensitized solar cell of the present embodiment was the same as that described in Embodiment 6, except that the ruthenium complex prepared by Embodiment 1 was substituted with the ruthenium complex prepared by Embodiment 4.

Comparative Embodiment 10
Preparation of a Dye-Sensitized Solar Cell

The process for preparing the dye-sensitized solar cell of the present comparative embodiment was the same as that described in Embodiment 6, except that the ruthenium complex prepared by Embodiment 1 was substituted with Z907.

Testing Methods and Results
Test for the Photoelectric Characteristics

The short circuit current ($J_{SC}$), open circuit voltage ($V_{OC}$), filling factor (FF), photoelectric conversion efficiency (η), and incident photon-to-current conversion efficiency (IPCE) of the dye-sensitized solar cells prepared by Embodiments 6-9 and Comparative Embodiment were measured under the illumination of AM 1.5 stimulated light. The testing results are shown in the following Table 1:

TABLE 1

Testing results of the dye and the dye-sensitized solar cell

| | Dye | $J_{SC}$ (mA/cm$^2$) | $V_{OC}$ (V) | FF | η (%) |
|---|---|---|---|---|---|
| Embodiment 6 | I-1 | 0.739 | 9.60 | 64.82 | 4.60 |
| Embodiment 7 | I-2 | 0.728 | 9.60 | 61.19 | 4.28 |
| Embodiment 8 | I-3 | 0.746 | 9.68 | 64.88 | 4.68 |
| Embodiment 9 | I-4 | 0.736 | 9.53 | 64.31 | 4.51 |
| Comparative embodiment | Z907 | 0.740 | 8.72 | 65.41 | 4.22 |

The testing results of Table 1 show that the short circuit current ($J_{SC}$), the open circuit voltage ($V_{OC}$) and the filling factor (FF) of the dye-sensitized solar cell prepared by the ruthenium complex of the present invention are improved, as compared with the dye-sensitized solar cell prepared by the Z907 dye. It means that the ruthenium complex of the present invention can improve the photoelectric conversion efficiency of the dye-sensitized solar cell.

In conclusion, the present invention is different from the prior arts in several ways, such as in purposes, methods and efficiency, or even in technology and research and design. Although the present invention has been explained in relation to its preferred embodiment, it is to be understood that many other possible modifications and variations can be made without departing from the scope of the invention as hereinafter claimed. Hence, the scope of the present invention should be defined as the claims appended hereto, and the foregoing examples should not be construed as in any way limiting the scope of the present invention.

Although the present invention has been explained in relation to its preferred embodiment, it is to be understood that many other possible modifications and variations can be made without departing from the scope of the invention as hereinafter claimed.

What is claimed is:

1. A ruthenium complex, represented by the following formula (I-3):

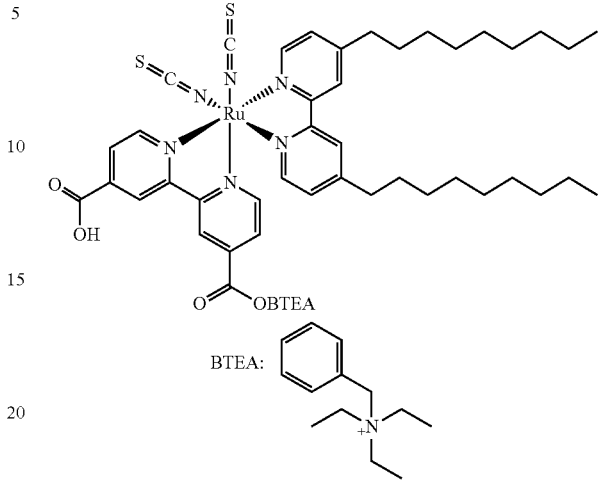

(I-3)

2. The ruthenium complex as claimed in claim 1, wherein the ruthenium complex is a dye compound for a dye-sensitized solar cell.

* * * * *